(12) United States Patent
Majeed et al.

(10) Patent No.: US 11,298,395 B2
(45) Date of Patent: Apr. 12, 2022

(54) ISOLATES FROM SPENT TURMERIC FOR THE MANAGEMENT OF RHEUMATOID ARTHRITIS

(71) Applicant: SAMI LABS LIMITED, Bangalore (IN)

(72) Inventors: Muhammed Majeed, Edison, NJ (US); Kalyanam Nagabhushanam, East Windsor, NJ (US); Beena Bhat, Bangalore (IN); Natarajan Sankaran, Bangalore (IN)

(73) Assignee: SAMI LABS LIMITED, Bangalore (IN)

( * ) Notice: Subject to any disclaimer, the term of this patent is extended or adjusted under 35 U.S.C. 154(b) by 9 days.

(21) Appl. No.: 16/632,953

(22) PCT Filed: Jul. 17, 2018

(86) PCT No.: PCT/US2018/042390
§ 371 (c)(1),
(2) Date: Jan. 22, 2020

(87) PCT Pub. No.: WO2019/022991
PCT Pub. Date: Jan. 31, 2019

(65) Prior Publication Data
US 2020/0164019 A1 May 28, 2020

(30) Foreign Application Priority Data
Jul. 24, 2017 (IN) .............................. 201741026215

(51) Int. Cl.
*A61K 36/9066* (2006.01)
*A61P 19/02* (2006.01)
*A61P 29/00* (2006.01)
*A61K 31/718* (2006.01)
*C07K 14/415* (2006.01)
*C08B 30/20* (2006.01)
*A61K 38/00* (2006.01)

(52) U.S. Cl.
CPC ........ *A61K 36/9066* (2013.01); *A61K 31/718* (2013.01); *A61P 19/02* (2018.01); *A61P 29/00* (2018.01); *C07K 14/415* (2013.01); *C08B 30/20* (2013.01); *A61K 38/00* (2013.01); *A61K 2236/331* (2013.01); *A61K 2236/39* (2013.01); *A61K 2236/51* (2013.01); *A61K 2236/53* (2013.01)

(58) Field of Classification Search
None
See application file for complete search history.

(56) References Cited

U.S. PATENT DOCUMENTS

| 10,323,227 | B2 * | 6/2019 | Majeed | ................ A61K 35/742 |
| 2014/0010903 | A1 * | 1/2014 | Madhavamenon | .... A61K 31/12 424/756 |
| 2016/0151440 | A1 * | 6/2016 | Gopi | ........................ A61K 9/08 424/756 |

FOREIGN PATENT DOCUMENTS

WO    WO 2017/195220    * 11/2017

OTHER PUBLICATIONS

Kumar, G. et al. Effect of Spent Tumeric on Kidney Glycoconjugates in Streptozotocin Induced Diabetic Rats. J of Diabetes & Metabolic Disorders 13:1-9, Aug. 4, 2014. (Year: 2014).*

* cited by examiner

*Primary Examiner* — Ralph J Gitomer (57) ABSTRACT

The present invention relates to a process for the isolation of bioactive components from spent turmeric (*Curcuma longa*) and compositions comprising said bioactive components. Further, the present invention also elucidates the potent anti-inflammatory activity of said bioactive compositions and therapeutic applications thereof in rheumatoid arthritis.

1 Claim, 5 Drawing Sheets

Fig.1

TPS: turmeric polysaccharide, TP: Turmeric Protein, ASA- Acetyl salicylic acid, *** p< 0.001

Fig.2

TPS: turmeric polysaccharide, TP: Turmeric Protein, ASA- Acetyl salicylic acid, *** p< 0.001

ISOLATES FROM SPENT TURMERIC FOR THE MANAGEMENT OF RHEUMATOID ARTHRITIS

CROSS-REFERENCE TO RELATED APPLICATIONS

This application is a US national phase application of PCT/US18/42390, filed on 17 Jul. 2018, claiming priority from Indian application no. 201741026215, filed on 24 Jul. 2017, the details of which is incorporated herein by reference.

BACKGROUND OF THE INVENTION

Field of the Invention

The present invention in general relates to *Curcuma longa* (turmeric). More specifically, the present invention relates to the isolation of bioactive glycoproteins and polysaccharides occurring with hydrophobic protein from spent turmeric and their potent anti-inflammatory activity and applications for the therapeutic management of rheumatoid arthritis.

Description of Prior Art

Spent turmeric constitutes the insoluble solids remaining after solvent extraction of turmeric powder (powdered dry rhizomes of *Curcuma longa*). It is considered as industrial waste. Nevertheless, the therapeutic potential of spent turmeric has been reported in art.

Gurusiddiah Suresh Kumar et al, "Effect of spent turmeric on kidney glycoconjugates in streptozotocin-induced diabetic rats", J Diabetes Metab Disord. 2014; 13: 78) disclose the beneficial effect of spent turmeric in controlling glycoconjugates such as glycoproteins and heparan sulfate related kidney complications during diabetes.

Han K H et al, "Spent turmeric reduces fat mass in rats fed a high-fat diet", Food Funct. 2016 April; 7(4):1814-24.

Preliminary investigations to characterize bioactive components of spent turmeric have yielded useful technical insights. Smitha S et al have reported a 34 kDa glycoprotein (beta-turmerin) from turmeric waste grits in Biochemie. 2009 September; 91 (9): 1156-1162

There is thus a technical need to explore the complete spectrum of bioactive components in spent turmeric and the nature of its therapeutic potential.

It is the principle objective of the present invention to disclose a novel, non-obvious and industrially applicable process scheme for the treatment of spent turmeric material in search of novel bioactives and the elucidation of their therapeutic potential.

It is another objective of the present invention to disclose immune stimulatory/anti-inflammatory glycoprotein and starch components of spent turmeric obtained by novel, non-obvious and industrially applicable process scheme for the treatment of spent turmeric.

The present invention fulfils aforesaid objectives and provides further related advantages.

SUMMARY OF THE INVENTION

A process for the isolation of bioactive components from spent turmeric (*Curcuma longa*) and compositions comprising said bioactive components are described. Further, the present invention also elucidates the potent anti-inflammatory activity of said bioactive compositions and therapeutic applications thereof in rheumatoid arthritis. A premium advantage of the present invention is the technical effect that the process of the present invention has resulted in glycoprotein comprising considerable amounts of rate limiting amino acids, cysteine and methionine which are rarely found in plant protein sources. The glycoprotein isolated using the process of the present invention may thus be considered "whole protein" from spent turmeric rhizomes.

The following terminology have been included to understand the scientific context of the instant invention as described in this specification.

A. Rate limiting amino acids: If a diet is inadequate in any essential amino acid, protein synthesis cannot proceed beyond the rate at which that amino acid is available. Such essential amino acids are called "rate limiting amino acid" or simply "limiting amino acid".

B. Total dissolved solids (TDS): Total dissolved solids (TDS) are a measure of the collective content of all inorganic and organic substances contained in a liquid. It can be suspended in forms such as Molecular, Ionized or Microgranular (colloidal sol).

C. Curcuminoids: Curcuminoids are natural chemical compounds in found in turmeric, including but not necessarily limited to curcumin, demethoxycurcumin and bisdemethoxycurcumin.

Other features and advantages of the present invention will become apparent from the following more detailed description, taken in conjunction with the accompanying images, which illustrate, by way of example, the principle of the invention.

BRIEF DESCRIPTION OF THE FIGURES

FIG. 4 shows photographs of the comparative ability of effective concentrations (100 mg/kg body weight, 200 mg/kg body weight and 400 mg/kg body weight) of spent turmeric polysaccharides and spent turmeric glycoprotein after 28 days treatment to reduce inflammation in paws of rats (measured by reduction in paw thickness and oedema)

induced by administering Complete adjuvant containing *Mycobacterium tuberculosis* (Adjuvant induced rheumatoid arthritis in rats).

DESCRIPTION OF THE MOST PREFERRED EMBODIMENTS

Figure 1:
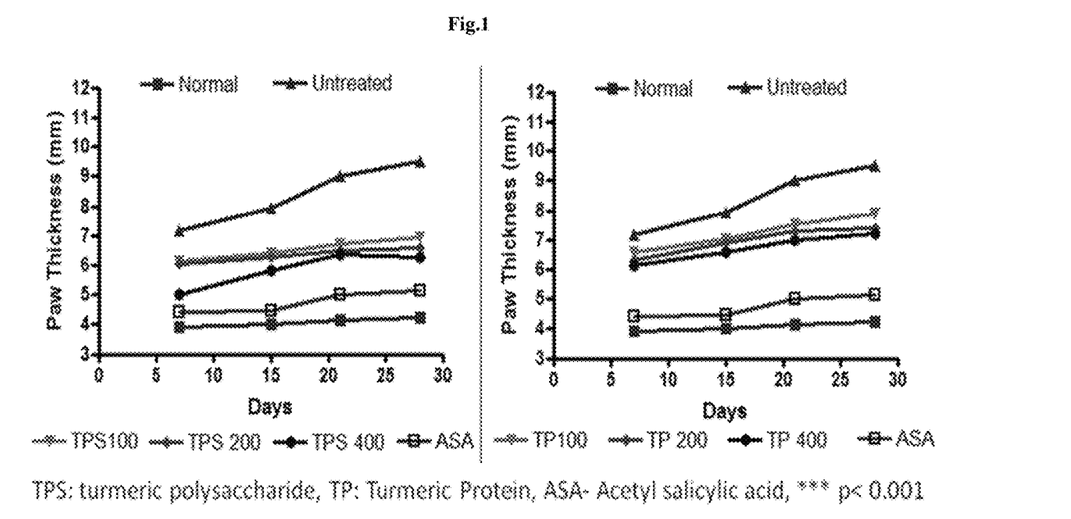
FIG. 1 shows the graphical representation of the comparative ability of effective concentrations (100 mg/kg body weight, 200 mg/kg body weight and 400 mg/kg body weight) of spent turmeric polysaccharides and spent turmeric glycoprotein to reduce inflammation in paws of rats (measured by reduction in paw thickness) induced by administering Complete adjuvant containing *Mycobacterium tuberculosis* (Adjuvant induced rheumatoid arthritis in rats).
Figure 2:
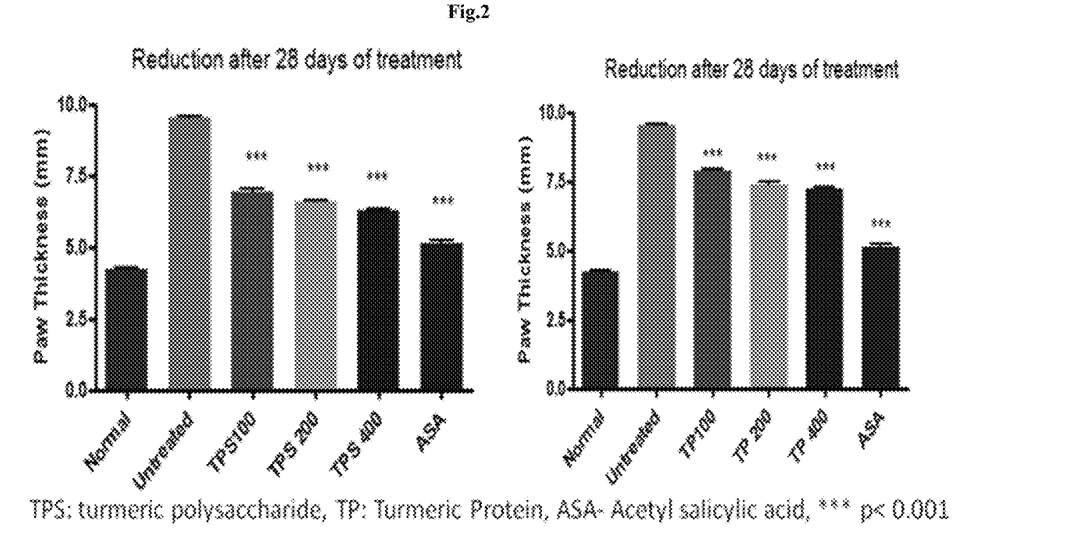
FIG. 2 shows the graphical representation of the comparative ability of effective concentrations (100 mg/kg body weight, 200 mg/kg body weight and 400 mg/kg body weight) of spent turmeric polysaccharides and spent turmeric glycoprotein after 28 days treatment to reduce inflammation in paws of rats (measured by reduction in paw thickness) induced by administering Complete adjuvant containing *Mycobacterium tuberculosis* (Adjuvant induced rheumatoid arthritis in rats).
Figure 3:
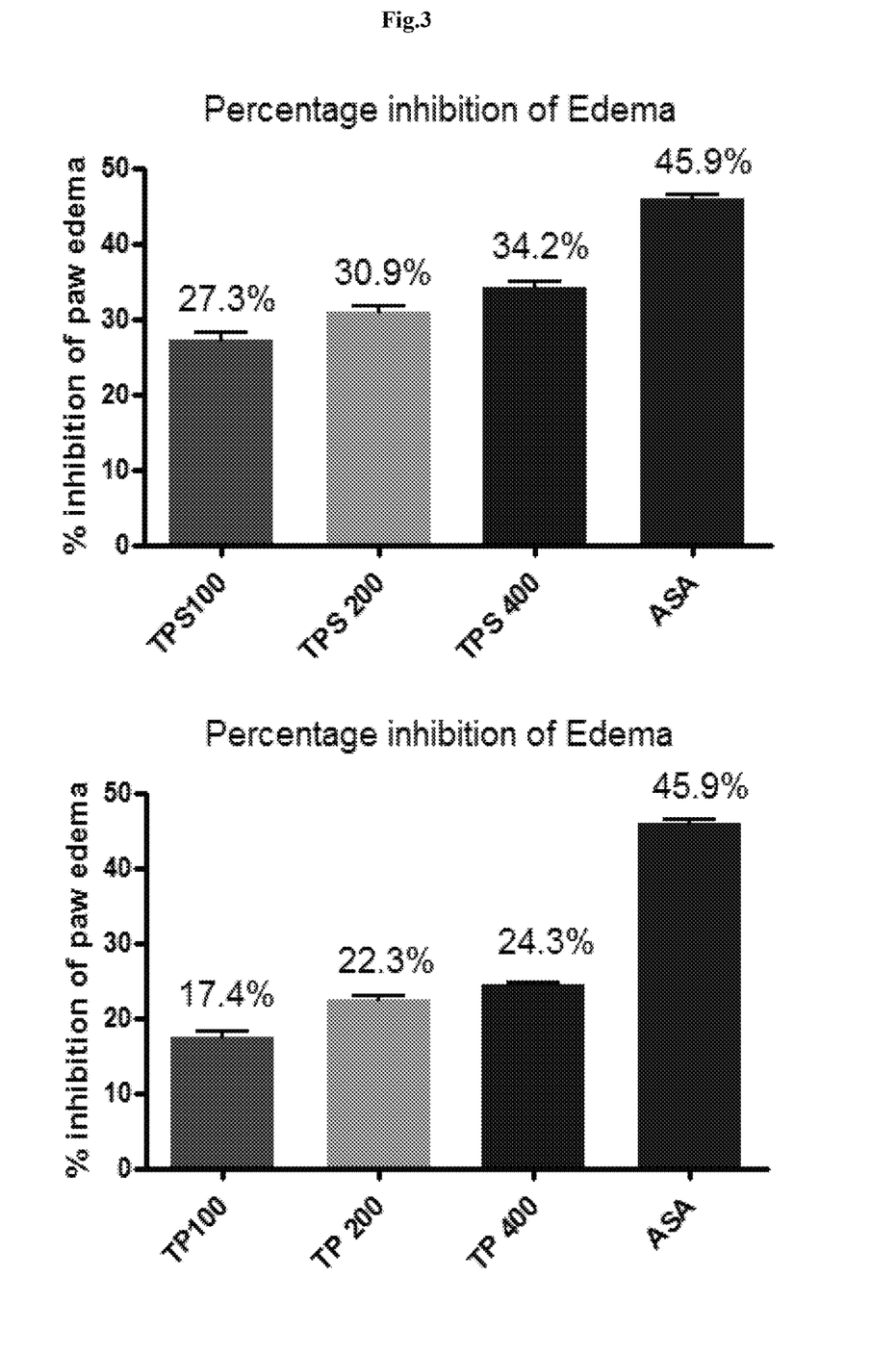
FIG. 3 shows the graphical representation of the comparative ability of effective concentrations (100 mg/kg body weight, 200 mg/kg body weight and 400 mg/kg body weight) of spent turmeric polysaccharides and spent turmeric glycoprotein after 28 days treatment to reduce inflammation in paws of rats (measured by reduction in paw oedema) induced by administering Complete adjuvant containing *Mycobacterium tuberculosis* (Adjuvant induced rheumatoid arthritis in rats).
Figure 4:
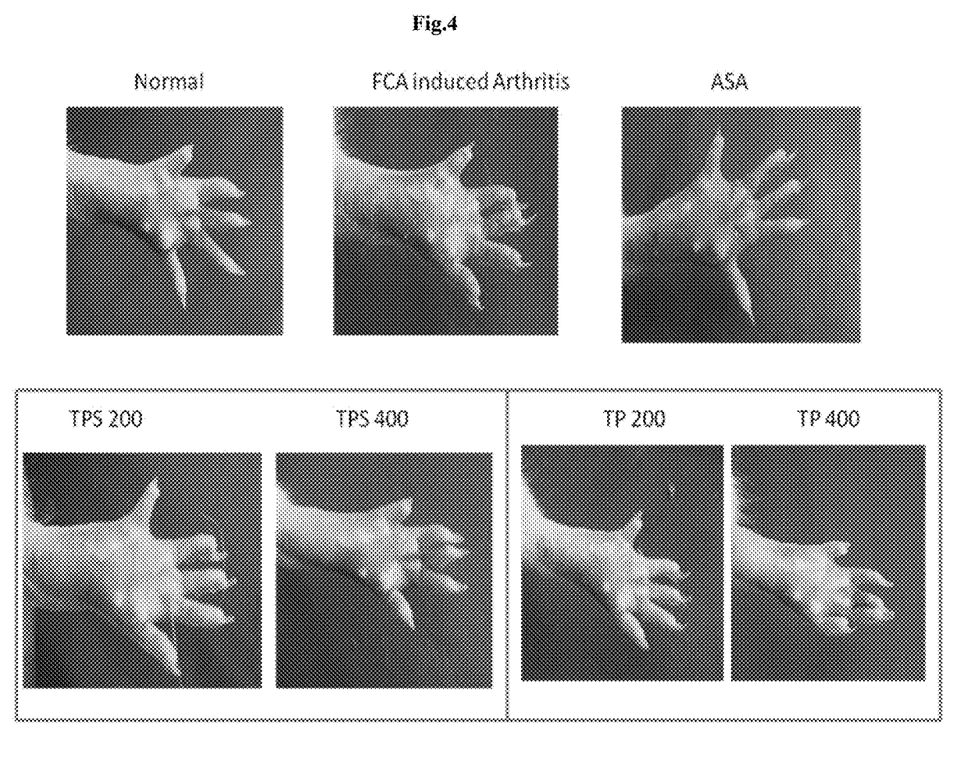
Figure 5:
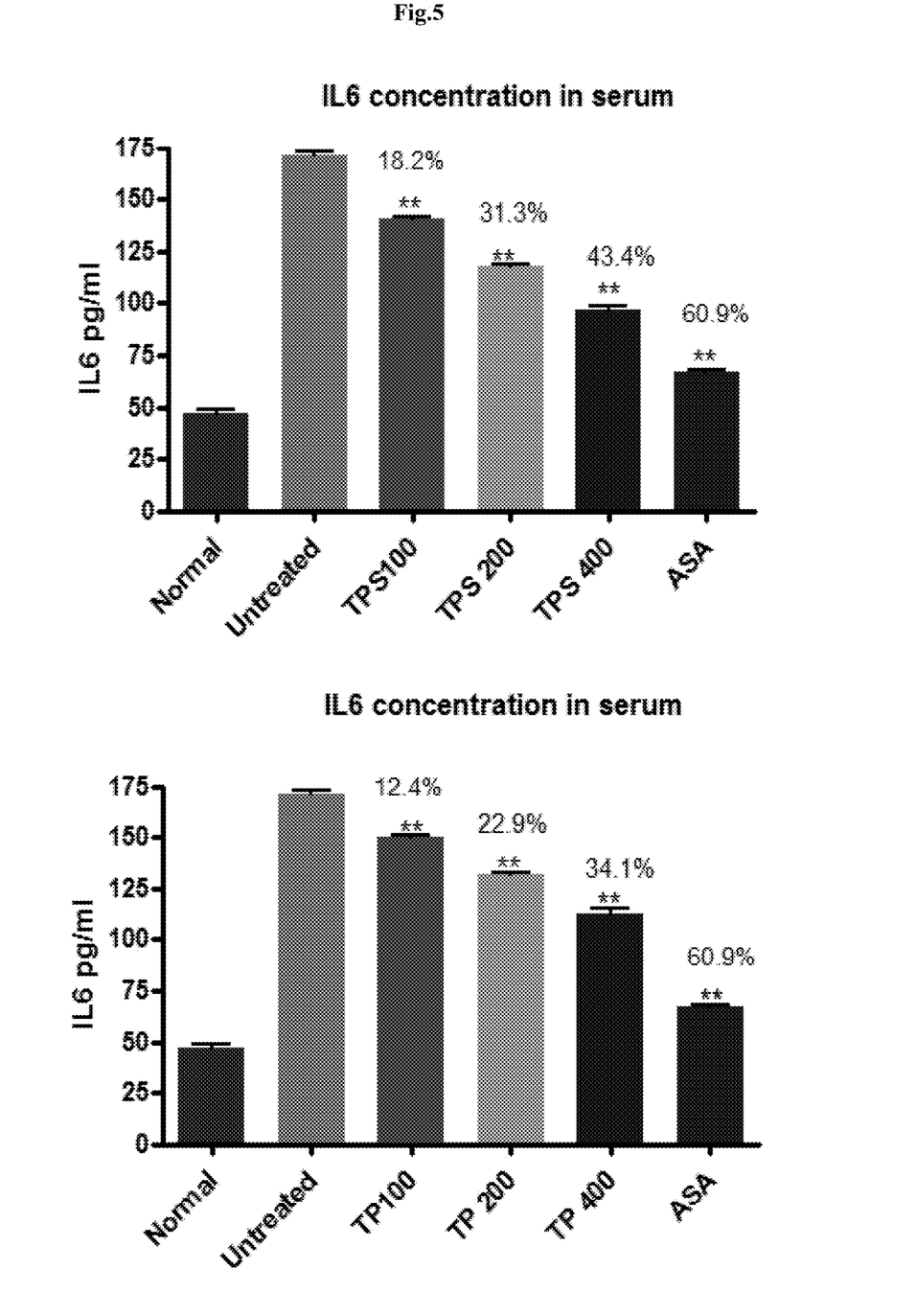
FIG. 5 shows the graphical representation of the comparative ability of effective concentrations (100 mg/kg body weight, 200 mg/kg body weight and 400 mg/kg body weight) of spent turmeric polysaccharides and spent turmeric glycoprotein after 28 days treatment to reduce serum inflammatory marker IL-6 following administration of Complete adjuvant containing *Mycobacterium tuberculosis* (Adjuvant induced rheumatoid arthritis in rats).
Figure 6:
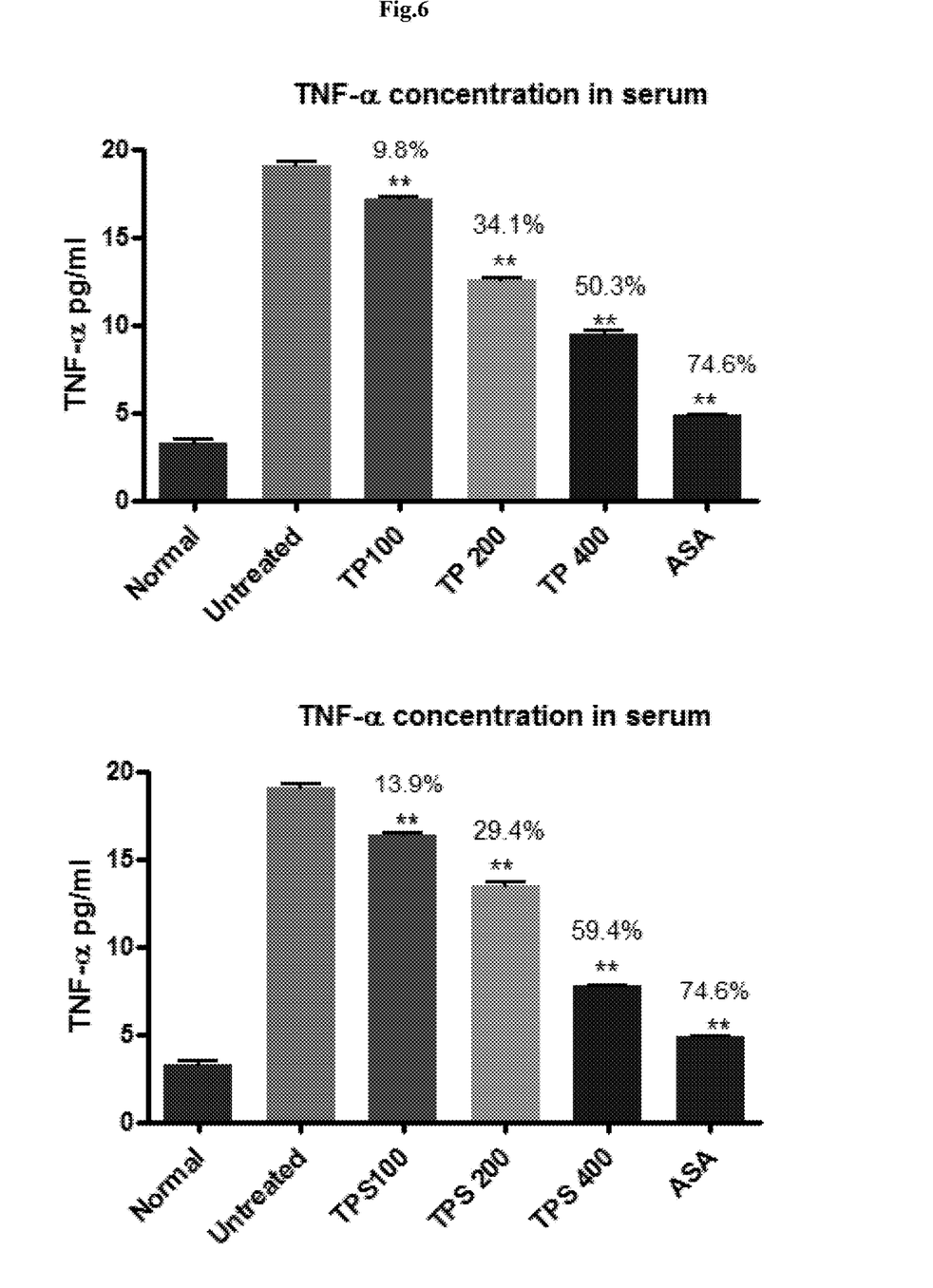
FIG. 6 shows the graphical representation of the comparative ability of effective concentrations (100 mg/kg body weight, 200 mg/kg body weight and 400 mg/kg body weight) of spent turmeric polysaccharides and spent turmeric glycoprotein after 28 days treatment to reduce serum inflammatory marker TNF-α following administration of Complete adjuvant containing *Mycobacterium tuberculosis* (Adjuvant induced rheumatoid arthritis in rats).

FIGS. 1, 2, 3, 4, 5 and 6

In the most preferred embodiment, the present invention relates to a method of water extraction of spent turmeric, said method comprising steps of,
  a) Extracting spent turmeric with water wherein ratio of spent turmeric and water is 1:10 at a temperature 65° C. for 6 hrs with occasional stirring to get the water extract of spent turmeric and spent turmeric material-2.
  b) Centrifuging the water extract of step (a) to trap sand or dust particles to obtain clear filtrate;
  c) Concentrating filtrate of step (b) to 20% total dissolved solids (TDS) under high vacuum followed by spray drying at 120° C. with the flow rate of 100 L/hr to get protein (glycoprotein) powder; and
  d) Subjecting spent turmeric material-2 of step (a) devoid of protein of step (c) to drying at 120° C. for 24 hours followed by powdering and sieving to get turmeric starch (polysaccharide) wherein polysaccharide occurs with hydrophobic protein.

In preferred embodiments, the ratio of spent turmeric and water is in the range of 1:10 to 1:50 in step (a).

In another most preferred embodiment, the present invention relates to a method of water extraction of spent turmeric, said method comprising steps of,
  a) Extracting spent turmeric with water wherein ratio of spent turmeric and water is 1:10 at a temperature 65° C. for 6 hrs with occasional stirring to get the water extract of spent turmeric and spent turmeric material-2;
  b) Centrifuging the water extract of step (a) to trap sand or dust particles to obtain clear filtrate;
  c) Concentrating the filtrate of step (b) at 60° C. with high vacuum to obtain concentrate and further cooling said concentrate;
  d) Adding organic solvent, in preferred embodiment acetone, to the concentrate of step (c) wherein ratio of organic solvent and concentrate, in preferred embodiment acetone and concentrate is 1:2, followed by occasional stirring, incubation at room temperature for 4 hours to form acetone precipitated protein and allowing said protein precipitate to completely settle down with supernatant above;
  e) Decanting the supernatant of step (d) without disturbing the protein precipitate followed by filtration, washing precipitate with acetone to remove moisture and filtering again;
  f) Drying protein precipitate of step (e) immediately at 60° C. with high vacuum to obtain fine protein (glycoprotein) powder,
  g) Subjecting spent turmeric material-2 of step (a) devoid of protein of step (f) to washing with soaking volume of Acetone and Methanol for 4 hrs each at 46° C. and 30° C. respectively to remove traces of curcuminoids and oxalic acid content to form washed spent turmeric material-2;
  h) Drying washed spent turmeric material-2 of step (g) for 24 hrs to remove residue solvents followed by powdering and sieving to get turmeric starch (polysaccharide) wherein polysaccharide occurs with hydrophobic protein.

In preferred embodiments, the ratio of spent turmeric and water is in the range of 1:10 to 1:50 in step (a).

In yet another most preferred embodiment, the present invention relates to a method of treating inflammation in mammals, said method comprising step of administering to said mammals effective amount of spent turmeric protein or spent turmeric starch, said protein and starch obtained by process comprising steps of
  a) Extracting spent turmeric with water wherein ratio of spent turmeric and water is 1:10 at a temperature 65° C. for 6 hrs with occasional stirring to get the water extract of spent turmeric and spent turmeric material-2.
  b) Centrifuging the water extract of step (a) to trap sand or dust particles to obtain clear filtrate;
  c) Concentrating filtrate of step (b) to 20% total dissolved solids (TDS) under high vacuum followed by spray drying at 120° C. with the flow rate of 100 L/hr to get protein (glycoprotein) powder; and
  d) Subjecting spent turmeric material-2 of step (a) devoid of protein of step (c) to drying at 120° C. for 24 hours followed by powdering and sieving to get turmeric starch (polysaccharide) wherein polysaccharide occurs with hydrophobic protein,
  to bring about effects of reducing inflammation.

In preferred embodiments, the ratio of spent turmeric and water is in the range of 1:10 to 1:50 in step (a).

In yet another most preferred embodiment, the present invention relates to a method of treating inflammation in mammals, said method comprising step of administering to said mammals effective amount of spent turmeric protein or spent turmeric starch, said protein and starch obtained by process comprising steps of
  a) Extracting spent turmeric with water wherein ratio of spent turmeric and water is 1:10 at a temperature 65° C. for 6 hrs with occasional stirring to get the water extract of spent turmeric and spent turmeric material-2;
  b) Centrifuging the water extract of step (a) to trap sand or dust particles to obtain clear filtrate;
  c) Concentrating the filtrate of step (b) at 60° C. with high vacuum to obtain concentrate and further cooling said concentrate;
  d) Adding organic solvent, in preferred embodiment acetone, to the concentrate of step (c) wherein ratio of organic solvent and concentrate, in preferred embodiment acetone and concentrate is 1:2, followed by occasional stirring, incubation at room temperature for 4 hours to form acetone precipitated protein and allowing said protein precipitate to completely settle down with supernatant above;

e) Decanting the supernatant of step (d) without disturbing the protein precipitate followed by filtration, washing precipitate with acetone to remove moisture and filtering again;

f) Drying protein precipitate of step (e) immediately at 60° C. with high vacuum to obtain fine protein (glycoprotein) powder;

g) Subjecting spent turmeric material-2 of step (a) devoid of protein of step (f) to washing with soaking volume of Acetone and Methanol for 4 hrs each at 46° C. and 30° C. respectively to remove traces of curcuminoids and oxalic acid content to form washed spent turmeric material-2; and h) Drying washed spent turmeric material-2 of step (g) for 24 hrs to remove residue solvents followed by powdering and sieving to get turmeric starch (polysaccharide) wherein polysaccharide occurs with hydrophobic protein, to bring about effects of reducing inflammation.

In yet another most preferred embodiment, the present invention relates to a method of treating rheumatoid arthritis in mammals, said method comprising step of administering to said mammals effective amount of spent turmeric protein or spent turmeric starch, said protein and starch obtained by process comprising steps of a) Extracting spent turmeric with water wherein ratio of spent turmeric and water is 1:10 at a temperature 65° C. for 6 hrs with occasional stirring to get the water extract of spent turmeric and spent turmeric material-2.

b) Centrifuging the water extract of step (a) to trap sand or dust particles to obtain clear filtrate;

c) Concentrating filtrate of step (b) to 20% total dissolved solids (TDS) under high vacuum followed by spray drying at 120° C. with the flow rate of 100 L/hr to get protein (glycoprotein) powder; and d) Subjecting spent turmeric material-2 of step (a) devoid of protein of step (c) to drying at 120° C. for 24 hours followed by powdering and sieving to get turmeric starch (polysaccharide) wherein polysaccharide occurs with hydrophobic protein, to bring about effects of reduction of symptoms of rheumatoid arthritis in said mammals including pain, swelling, oedema and reduction in serum markers of IL-6 and TNF-α.

In preferred embodiments, the ratio of spent turmeric and water is in the range of 1:10 to 1:50 in step (a).

In yet another most preferred embodiment, the present invention relates to a method of treating rheumatoid arthritis in mammals, said method comprising step of administering to said mammals effective amount of spent turmeric protein or spent turmeric starch, said protein and starch obtained by process comprising steps of a) Extracting spent turmeric with water wherein ratio of spent turmeric and water is 1:10 at a temperature 65° C. for 6 hrs with occasional stirring to get the water extract of spent turmeric and spent turmeric material-2;

b) Centrifuging the water extract of step (a) to trap sand or dust particles to obtain clear filtrate;

c) Concentrating the filtrate of step (b) at 60° C. with high vacuum to obtain concentrate and further cooling said concentrate;

d) Adding organic solvent, in preferred embodiment acetone, to the concentrate of step (c) wherein ratio of organic solvent and concentrate, in preferred embodiment acetone and concentrate is 1:2, followed by occasional stirring, incubation at room temperature for 4 hours to form acetone precipitated protein and allowing said protein precipitate to completely settle down with supernatant above;

e) Decanting the supernatant of step (d) without disturbing the protein precipitate followed by filtration, washing precipitate with acetone to remove moisture and filtering again;

f) Drying protein precipitate of step (e) immediately at 60° C. with high vacuum to obtain fine protein (glycoprotein) powder;

g) Subjecting spent turmeric material-2 of step (a) devoid of protein of step (f) to washing with soaking volume of Acetone and Methanol for 4 hrs each at 46° C. and 30° C. respectively to remove traces of curcuminoids and oxalic acid content to form washed spent turmeric material-2; and h) Drying washed spent turmeric material-2 of step (g) for 24 hrs to remove residue solvents followed by powdering and sieving to get turmeric starch (polysaccharide) wherein polysaccharide occurs with hydrophobic protein, to bring about effects of reduction of symptoms of rheumatoid arthritis in said mammals including pain, swelling, oedema and reduction in serum markers of IL-6 and TNF-α.

In preferred embodiments, the ratio of spent turmeric and water is in the range of 1:10 to 1:50 in step (a).

In yet another most preferred embodiment, the present invention relates to a protein composition obtained from spent turmeric material, said protein composition obtained by the water extraction of spent turmeric comprising steps of a) Extracting spent turmeric with water wherein ratio of spent turmeric and water is 1:10 at a temperature 65° C. for 6 hrs with occasional stirring to get the water extract of spent turmeric and spent turmeric material-2.

b) Centrifuging the water extract of step (a) to trap sand or dust particles to obtain clear filtrate; and c) Concentrating filtrate of step (b) to 20% total dissolved solids (TDS) under high vacuum followed by spray drying at 120° C. with the flow rate of 100 L/hr to get protein (glycoprotein) powder.

In yet another most preferred embodiment, the present invention relates to a protein composition obtained from spent turmeric material, said protein composition obtained by the water extraction of spent turmeric comprising steps of a) Extracting spent turmeric with water wherein ratio of spent turmeric and water is 1:10 at a temperature 65° C. for 6 hrs with occasional stirring to get the water extract of spent turmeric and spent turmeric material-2;

b) Centrifuging the water extract of step (a) to trap sand or dust particles to obtain clear filtrate;

c) Concentrating the filtrate of step (b) at 60° C. with high vacuum to obtain concentrate and further cooling said concentrate;

d) Adding organic solvent, in preferred embodiment acetone, to the concentrate of step (c) wherein ratio of organic solvent and concentrate, in preferred embodiment acetone and concentrate is 1:2, followed by occasional stirring, incubation at room temperature for 4 hours to form acetone precipitated protein and allowing said protein precipitate to completely settle down with supernatant above;

e) Decanting the supernatant of step (d) without disturbing the protein precipitate followed by filtration, washing precipitate with acetone to remove moisture and filtering again; and f) Drying protein precipitate of step (e) immediately at 60° C. with high vacuum to obtain fine protein (glycoprotein) powder.

In yet another most preferred embodiment, the present invention relates to a polysaccharide composition comprising polysaccharides with hydrophobic protein, said composition obtained from spent turmeric through process comprising steps of,
a) Extracting spent turmeric with water wherein ratio of spent turmeric and water is 1:10 at a temperature 65° C. for 6 hrs with occasional stirring to get the water extract of spent turmeric and spent turmeric material-2.
b) Centrifuging the water extract of step (a) to trap sand or dust particles to obtain clear filtrate;
c) Concentrating filtrate of step (b) to 20% total dissolved solids (TDS) under high vacuum followed by spray drying at 120° C. with the flow rate of 100 L/hr to get protein (glycoprotein) powder; and
d) Subjecting spent turmeric material-2 of step (a) devoid of protein of step (c) to drying at 120° C. for 24 hours followed by powdering and sieving to get turmeric starch (polysaccharide) wherein polysaccharide occurs with hydrophobic protein.

In preferred embodiments, the ratio of spent turmeric and water is in the range of 1:10 to 1:50 in step (a).

In yet another most preferred embodiment, the present invention relates to a polysaccharide composition comprising polysaccharides with hydrophobic protein, said composition obtained from spent turmeric through process comprising steps of,
a) Extracting spent turmeric with water wherein ratio of spent turmeric and water is 1:10 at a temperature 65° C. for 6 hrs with occasional stirring to get the water extract of spent turmeric and spent turmeric material-2;
b) Centrifuging the water extract of step (a) to trap sand or dust particles to obtain clear filtrate;
c) Concentrating the filtrate of step (b) at 60° C. with high vacuum to obtain concentrate and further cooling said concentrate;
d) Adding organic solvent, in preferred embodiment acetone, to the concentrate of step (c) wherein ratio of organic solvent and concentrate, in preferred embodiment acetone and concentrate is 1:2, followed by occasional stirring, incubation at room temperature for 4 hours to form acetone precipitated protein and allowing said protein precipitate to completely settle down with supernatant above;
e) Decanting the supernatant of step (d) without disturbing the protein precipitate followed by filtration, washing precipitate with acetone to remove moisture and filtering again;
f) Drying protein precipitate of step (e) immediately at 60° C. with high vacuum to obtain fine protein (glycoprotein) powder;
g) Subjecting spent turmeric material-2 of step (a) devoid of protein of step (f) to washing with soaking volume of Acetone and Methanol for 4 hrs each at 46° C. and 30° C. respectively to remove traces of curcuminoids and oxalic acid content to form washed spent turmeric material-2;
h) Drying washed spent turmeric material-2 of step (g) for 24 hrs to remove residue solvents followed by powdering and sieving to get turmeric starch (polysaccharide) wherein polysaccharide occurs with hydrophobic protein.

In yet another most preferred embodiment, the present invention relates to a plant protein composition, said protein composition obtained from spent turmeric characterised in that said protein composition comprises rate limiting amino acids cysteine and methionine.

In yet another most preferred embodiment, the present invention relates to a plant polysaccharide composition (starch), said polysaccharide composition obtained from spent turmeric characterised as resistant starch having 90% glucose residues linked by $\alpha$, 1-4 linkage (Amylose) and $\alpha$, 1-6 linkage (Amylopectin) occurring along with hydrophobic glycoprotein.

The aforesaid most preferred embodiments incorporating the technical features and technical effects of instant invention, are explained through illustrative examples herein under.

Example 1

One kg spent Turmeric was extracted with water (1:10 ratio) at 65° C. for 6 hrs with occasional stirring to obtain the water extract of spent turmeric and spent turmeric portion-2. After 6 hrs extraction, immediately the water extract was filtered through Hyflo bedded centrifuge to trap any sand or dust particles. 7 L filtrate obtained was concentrated to 20% total dissolved solids (TDS) with high vacuum. Further, the water extract was spray dried at 120° C. with the flow rate of 100 L/hr. Light Brown coloured powder was obtained with 4% yield. The crude water extract sample was analyzed by CHNS (Carbon, Hydrogen, Nitrogen, and Sulphur) analysis and Bradford method to estimate the total percentage of protein. The total protein percentage was found to be 6.73% by CHNS method & 3% by Bradford method (Assay of protein). Further, amino acid analysis indicated that spent turmeric protein consisted of 18 important amino acids with high percentage of Aspartic acid and Glutamic acid (1030 mg/100 gm and 985 mg/100 gm respectively) and the total percentage of protein found to be 4.91 gm/100 gm of spray dried water extract. Cysteine and Methionine are two rate limiting amino acids which are rarely found in plant source of protein. The glycoprotein from spent turmeric consisted of 50 mg of cysteine and 110 mg of methionine/100 gm of glycoprotein. The presence of these amino acids in spent turmeric glycoprotein makes it a "whole Protein". Spent portion-2 was further dried in hot air oven at 120° C. for 24 hrs, made into fine powder and sieved through 80 number mesh screen to obtain starch from spent turmeric. Turmeric starch was produced with 80% yield and the total percentage of starch was found to be 49%. Spent turmeric starch (polysaccharide) occurred with hydrophobic protein.

Example 2

Protein Enrichment Via Precipitation Using Organic Solvent (Acetone as an Illustrative Example)

One kg spent Turmeric was extracted with water (1:10 ratio) at 65° C. for 6 hrs with occasional stirring to obtain the water extract of spent turmeric and spent portion-2. After 6 hrs extraction, immediately the water extract was filtered through Hyflo bedded centrifuge to trap any sand or dust particles. The 7 L water filtrate obtained was concentrated to one litre using at 60° C. with high vacuum. After cooling, 1:2 ratio of acetone was added to water extract with occasional stirring, kept for incubation at room temperature for 4 hrs and the precipitate was allowed to completely settle down. The supernatant was carefully decanted without disturbing the precipitate and filtered through Whatmann filter paper. The moisture in the precipitate was removed by washing with acetone followed by filtering through Whatmann filter paper. The resultant protein precipitate was immediately dried at 60° C. with high vacuum until it became fine cream colour protein powder. The powder was obtained with 4% yield and the sample was analyzed by CHNS analysis to estimate the total percentage of protein. The total protein percentage found to be 3 gm/100 gm. CHNS analysis showed 9% w/w of protein whereas amino acid analysis showed 8.595% w/w protein. The amino acid analysis was done by performing acid hydrolysis using 6N HCl at 110° C. for 24 hrs, followed by oxidation of HCl samples by performic acid (for determination of cysteine and Methionine as cysteic acid and methionine sulfone). NorLeu dilution buffer was added to the hydrolyzed sample, vortexed and spin down. 50 µl hydrolysate was loaded to L-8800 Hitachi analyzer consisting of ion exchange chromatography column to separate amino acids using sodium citrate buffer system followed by post column Ninhydrin reaction detection system (Separation, detection and analysis of amino acids). Amino acid analysis indicated that protein from spent turmeric consisted of 18 important amino acids with high amounts (% w/w) of Aspartic acid and Glutamic acid (1170 mg/100 gm and 1044 mg/100 g) and the total percentage of protein found to be 8.595 gm/100 gm of dried protein powder. Spent portion-2 is washed with soaking volume of Acetone and Methanol for 4 hrs each at 46° C. and 30° C. respectively to remove traces of curcuminoids and oxalic acid content. Spent turmeric starch Acetone mother liquor (filtrate) contains 0.2% yield with 16% assay of total Curcuminoids w/w (Curcumin—11.99%, demethoxycurcumin—2.68% and bisdemethoxycurcumin—1.50%). Starch rich spent turmeric was then dried in hot air oven for 24 hrs to remove residual solvents, made into fine powder and sieved through 80 number mesh screen. Turmeric starch was produced with 75% yield and the total percentage of starch found to be 60%. Polysaccharide (starch) from spent turmeric occurred with hydrophobic protein.

Total Starch Analysis:

Starch from spent turmeric is pre dissolved by stirring the sample with 2 M KOH at 4° C., followed by neutralisation with sodium acetate buffer and hydrolysis with α-amylase. Thermostable α-amylase hydrolyses starch into soluble branched and unbranched maltodextrins. Amyloglucocidase quantitatively hydrolyses maltodextrins to D-glucose. D-glucose is oxidised to D-gluconate with the release of hydrogen peroxide, which is quantitatively measured in a colorimetric reaction employing peroxidase and the production of a quinoneimine dye Glucose Percentage & Linkage Pattern:

Glycosyl composition analysis and Glycosyl linkage analysis was performed by combined gas chromatography and mass spectrometry. For glycosyl composition analysis, the sample was subjected to acidic methanolysis using methanolic HCl for 17 h at 80° C. to produce monosaccharide methyl glycoside which was analyzed by GC-MS. For glycosyl linkage analysis, the sample was permethylated, depolymerized, reduced and acetylated and the resultant partially methylated alditol acetates were analyzed by GC-MS. Starch from spent turmeric comprised about 90% of the glucose and also showed four linked glucose residues with 90% of the total peak area, that represented that the sample was enriched in starch The nutritional profile of 100 gm spent turmeric polysaccharides obtained by the process (solvent based extraction, illustratively acetone) of the instant invention is represented in Table A.

TABLE A

| S. No | Nutrients | Amount (w/w) in gms |
|---|---|---|
| 1 | Protein | 9.0-9.5 |
| 2 | Resistant starch | 55-60 |
| 3 | Dietary Fibre | 30-35 |
| 4 | Fat | 0.12-0.19 |
| 5 | Calories | 349.43 Kcal |
| 6 | Vitamin C | 0.005 |
| 7 | Calcium | 0.27-0.33 |
| 8 | Iron | 0.14-0.16 |
| 9 | Magnesium | 0.17-0.18 |
| 10 | Potassium | 0.75-0.78 |
| 11 | Sodium | 0.011-0.11 |
| 12 | Zinc | 0.001-0.002 |
| 13 | Manganese | 0.003-0004 |
| 14 | Copper | 0.0005-0.0009 |
| 15 | Phosphorous | 0.1-0.2 |

The nutritional profile of 100 gm spent turmeric polysaccharides obtained by the process (only water extraction without the use of solvents) of the instant invention is represented in Table B.

TABLE B

| S. No | Nutrients | Amount (w/w) in gms |
|---|---|---|
| 1 | Protein | 9.48 |
| 2 | Resistant starch | 49 |
| 3 | Dietary Fibre | 65.5 |
| 4 | Fat | 0.1 |
| 5 | Calories | 233.99 Kcal |
| 7 | Calcium | 0.4 |
| 8 | Iron | 0.066 |
| 9 | Magnesium | 0.24 |
| 10 | Potassium | 1.65 |
| 11 | Sodium | 0.031 |
| 12 | Zinc | 0.001 |
| 13 | Manganese | 0.003 |
| 14 | Copper | 0.0005 |
| 15 | Phosphorous | 0.21 |

The nutritional profile of 100 gms of spent turmeric glycoprotein obtained by the process (solvent based extraction, illustratively acetone) of the instant invention is represented in Table C.

TABLE C

| S. No | Nutrients | Amount (w/w) in gms |
|---|---|---|
| 1 | Protein | 9-10 |
| 2 | Carbohydrates | 53 |
| 3 | Dietary Fibre | 29 |
| 4 | Fat | 0.17 |
| 5 | Calories | 321.7 Kcal |
| 6 | Vitamin C | 0.01 |
| 7 | Calcium | 0.22 |
| 8 | Iron | 0.11 |
| 9 | Magnesium | 1.30 |
| 10 | Potassium | 4.31 |
| 11 | Sodium | 0.056 |
| 12 | Zinc | 0.006 |
| 13 | Manganese | 0.019 |
| 14 | Copper | 0.001 |
| 15 | Phosphorous | 0.9 |

The amino acid profile of spent turmeric glycoprotein obtained by the process (solvent based extraction, illustratively acetone) of the instant invention is represented in Table D.

TABLE D

| S. No | Amino acid | Amount in mg (100 gm) |
|---|---|---|
| 1 | Aspartic acid | 1170 |
| 2 | Threonine | 427 |
| 3 | Serine | 604 |
| 4 | Glutamic acid | 1044 |
| 5 | proline | 258 |
| 6 | Glycine | 768 |
| 7 | Alanine | 566 |
| 8 | valine | 616 |
| 9 | Iso Leucine | 470 |
| 10 | Leucine | 724 |
| 11 | Tyrosine | 282 |
| 12 | Phenylalanine | 364 |
| 13 | Histidine | 158 |
| 14 | Lysine | 274 |
| 15 | Arginine | 340 |
| 16 | cysteine | 100 |
| 17 | Methionine | 220 |
| 18 | Tryptophan | 210 |

The nutritional Profile of 100 gm spent turmeric glycoprotein (aqueous extract without any solvent) is represented in Table E.

TABLE E

| S. No | Nutrients | Amount (w/w) in gms |
|---|---|---|
| 1 | Protein | 6.73 |
| 2 | Carbohydrates | 47 |
| 3 | Dietary Fibre | 52 |
| 4 | Fat | 0.08 |
| 5 | Calories | 219.34 Kcal |
| 6 | Vitamin C | 0.01 |
| 7 | Calcium | 0.17 |
| 8 | Iron | 0.01 |
| 9 | Magnesium | 1.01 |
| 10 | Potassium | 13.59 |
| 11 | Sodium | 0.31 |
| 12 | Zinc | 0.02 |
| 13 | Manganese | 0.01 |
| 14 | Copper | 0.001 |
| 15 | Phosphorous | 1.33 |

The amino acid profile of aqueous extract of (aqueous extract without any solvent) spent turmeric is represented in Table F.

TABLE F

| S. No | Amino acid | Amount in mg (100 gm) |
|---|---|---|
| 1 | Aspartic acid | 1030 |
| 2 | Glutamic acid | 985 |
| 3 | Serine | 160 |
| 4 | Threonine | 160 |
| 5 | proline | 135 |
| 6 | Glycine | 225 |
| 7 | Alanine | 170 |
| 8 | Valine | 295 |
| 9 | Iso Leucine | 100 |
| 10 | Leucine | 165 |
| 11 | Tyrosine | 750 |
| 12 | Phenylalanine | 125 |
| 13 | Histidine | 90 |
| 14 | Lysine | 70 |
| 15 | Arginine | 210 |
| 16 | cysteine | 50 |
| 17 | Methionine | 110 |
| 18 | Tryptophan | 80 |

Example III

In Vitro Anti-Inflammatory Activity

The anti-inflammatory activities of spent turmeric protein (TP) and spent turmeric polysaccharides (starch) (TPS) on cytokine production by lipopolysaccharide stimulated (LPS=100 ng/ml for 24 hours) Human Monocytic cell line THP-1 or Murine macrophage cell line J774 are represented in Table 1. Cytokine TNF-α was measured in cell supernatants.

TABLE 1

| Concentration μg/ml | % Inhibition |
|---|---|
| SPENT TURMERIC POLYSACCARIDE (TPS) | |
| 50.00 | 41.38 |
| 25.00 | 25.22 |
| 12.50 | 7.07 |
| SPENT TURMERIC PROTEIN (TP) | |
| 50.00 | 50.7 |
| 25.00 | 54.52 |
| CURCUMINOIDS (95%) Curcumin C3 Complex ® | |
| 0.38 | 36.29 |
| 0.19 | 33.32 |

Results: Spent turmeric polysaccharide showed 41.3% inhibition of TNF-α release while spent turmeric glycoprotein inhibited TNF-α by 50.7%.

Example IV

In Vivo Biological (Anti-Arthritic) Activity

Male Wistar rats weighing 150-180 kg were orally dosed with 100, 200 and 400 mg/kg of spent turmeric polysaccharide from day 1-day 28. The animals were given intradermal injection of Freund's complete adjuvant in the paw at a dosage level of 0.1 ml on days 7, 15, 21 and 28 of the study to induce arthritis. Oedema induced by the adjuvant was measured as increase in paw volumes on days 7, 15, 21 and 28. At the end of the study, animals were sacrificed and blood and tissue collected for analyzing the inflammatory parameters. The inflammatory parameters studied included, a. Inflammation in the paws b. Blood Biochemistry c. Lipid Per oxidation d. Reduced Glutathione in serum e. Superoxide dismutase activity in serum f. Levels of Acid and Alkaline phosphatase g. TNF-α levels h. IL6 levels Results:

a. Significant reduction in paw edema (inflammation) was observed upon treatment with spent turmeric glycoprotein and polysaccharides with concurrent reduction of serum markers of inflammation IL-6, TNF-α (FIGS. 1, 2, 3, 4, 5 and 6).

b. Further, treatment with spent turmeric proteins and polysaccharides reduced lipid per oxidation, superoxide dismutase activity and increased the concentration of reduced glutathione in serum of arthritic animals (Table 2).

TABLE 2

| TREATMENT GROUPS | LIPID PEROXIDATION malondialdehyde formed (nm/g tissue) | SUPEROXIDE DISMUTASE (g activity in tissue/min) | Reduced Glutathione (μg/g tissue) |
|---|---|---|---|
| Normal control | 13.76 ± 0.22 | 13.86 ± 0.06 | 701.35 ± 1.35 |
| TPS 100 | 33.38 ± 0.20 | 36.05 ± 0.01 | 393.94 ± 2.02 |
| TPS 200 | 23.20 ± 0.25 | 29.59 ± 0.01 | 481.40 ± 1.89 |
| TPS 400 | 19.07 ± 0.08 | 16.97 ± 0.01 | 588.71 ± 1.33 |
| TP 100 | 37.96 ± 0.09 | 38.66 ± 0.01 | 360.42 ± 1.61 |
| TP 200 | 25.63 ± 0.11 | 30.55 ± 0.01 | 435.61 ± 0.99 |
| TP 400 | 20.17 ± 0.07 | 17.47 ± 0.01 | 543.37 ± 0.54 |
| ASA (Acetyl salicylic acid) | 18.19 ± 0.10 | 16.39 ± 0.01 | 595.69 ± 0.64 |
| Disease control | 43.95 ± 0.21 | 40.43 ± 0.01 | 277.86 ± 1.86 | c. Spent turmeric proteins and polysaccharides also reduced the high levels of acid phosphatase (ACP) and alkaline phosphatase (ALP) in arthritic animals (Table 3).

TABLE 3

| TREATMENT GROUPS | ALP (IU/ml) | ACP (IU/ml) |
|---|---|---|
| Normal control | 88.23 ± 0.88 | 4.42 ± 0.05 |
| TPS100 | 216.24 ± 1.55 | 16.27 ± 0.04 |
| TPS200 | 142.73 ± 0.88 | 10.41 ± 0:04 |
| TPS400 | 106.14 ± 1.54 | 8.33 ± 0.04 |
| TP 100 | 243.24 ± 1.11 | 16.27 ± 0.09 |
| TP 200 | 152.30 ± 1.52 | 11.13 ± 0.06 |
| TP 400 | 113.35 ± 1.44 | 9.06 ± 0.20 |
| ASA (Acetyl salicylic acid) | 104.18 ± 0.94 | 6.71 ± 0.06 |
| Disease control | 252.77 ± 0.32 | 17.43 ± 0.13 | d. Spent turmeric proteins and polysaccharides also restored the elevated numbers of blood cells (RBCs, WBCs and platelets) in arthritic animals to normal (Table 4).

TABLE 4

| STUDY GROUPS | White blood corpuscles-WBCs (Cells/μl) | Red blood corpuscles-RBCs (10⁶ Cells /μl) | Platelets (10⁹/L) |
|---|---|---|---|
| Normal control | 7550.0 ± 84.66 | 4.85 ± 0.06 | 165 ± 4.28 |
| TPS100 | 16275.0 ± 198.22 | 4.02 ± 0.04 | 260 ± 3.65 |
| TPS200 | 11650.0 ± 76.38 | 4.50 ± 0.04 | 231 ± 6.30 |
| TPS400 | 8050.0 ± 243.24 | 4.68 ± 0.05 | 208 ± 7.83 |
| TP100 | 19200.0 ± 208.17 | 3.80 ± 0.06 | 281 ± 4.58 |
| TP200 | 12400.0 ± 186.19 | 4.28 ± 0.06 | 245 ± 4.28 |
| TP400 | 19200.0 ± 208.17 | 3.80 ± 0.06 | 281 ± 4.58 |
| ASA (Acetyl salicylic acid) | 7800.0 ± 85.63 | 4.70 ± 0.04 | 232 ± 2.65 |
| Disease control | 23900.0 ± 322.49 | 3.33 ± 0.05 | 329 ± 6.51 |

Other modifications and variations to the invention will be apparent to those skilled in the art from the foregoing disclosure and teachings. Thus, while only certain embodiments of the invention have been specifically described herein, it will be apparent that numerous modifications may be made thereto without departing from the spirit and scope of the invention.

We claim:

1. A method of treating rheumatoid arthritis in mammals, said method comprising step of administering to said mammals effective amounts of spent turmeric protein or spent turmeric starch, said protein and starch obtained by process comprising steps of a) Extracting spent turmeric with water wherein ratio of spent turmeric and water is from about 1:10 to about 1:50, at a temperature 65° C. for 6 hours with occasional stirring to get water extract of spent turmeric and a residual material, wherein the residual material is spent turmeric material-2;

b) Centrifuging the water extract of step (a) to trap sand or dust particles to obtain a clear filtrate;

c) Concentrating the clear filtrate of step (b) at 60° C. with high vacuum to obtain a concentrate and further cooling said concentrate;

d) Adding acetone, to the concentrate of step (c) wherein ratio of acetone and concentrate, is 1:2, followed by occasional stirring, incubation at room temperature for 4 hours to form acetone precipitated protein and allowing the precipitated protein to completely settle down with a supernatant above;

e) Decanting the supernatant of step (d) without disturbing the precipitated protein followed by filtration, washing the precipitated protein with acetone to remove moisture and filtering again;

f) Drying protein precipitate of step (e) immediately at 60° C. with high vacuum to obtain fine protein (glycoprotein) powder as an extract, wherein the extract reduces inflammation and symptoms of rheumatoid arthritis in said mammals including pain, swelling, oedema and reduction in serum markers of IL-6 and TNF-α;

g) Subjecting the residual spent turmeric material-2 of step (a) devoid of protein of step (f) to washing with soaking volume of Acetone and Methanol for 4 hours each at 46° C. and 30° C. respectively to remove traces of curcuminoids and oxalic acid content to form washed spent turmeric material-2; and h) Drying washed spent turmeric material-2 of step (g) for 24 hours to remove residue solvents followed by powdering and sieving to get turmeric starch (polysaccharide) as an extract wherein polysaccharide is attached to hydrophobic protein, wherein the extract reduces inflammation and symptoms of rheumatoid arthritis in said mammals including pain, swelling, oedema and reduction in serum markers of IL-6 and TNF-α.

* * * * *